(12) United States Patent
Nelson

(10) Patent No.: US 6,179,798 B1
(45) Date of Patent: Jan. 30, 2001

(54) ADJUSTMENT SPLINT ASSEMBLY

(76) Inventor: Mico Nelson, 66 Hilltop Dr., Charlestown, RI (US) 02813

( * ) Notice: Under 35 U.S.C. 154(b), the term of this patent shall be extended for 0 days.

(21) Appl. No.: 09/587,829

(22) Filed: Jun. 6, 2000

(51) Int. Cl.[7] .................................................. A61F 5/00
(52) U.S. Cl. .................................. 602/5; 602/23; 602/26; 602/27; 128/882
(58) Field of Search .................................. 128/869, 882; 119/714, 817; 602/23, 26, 27

(56) References Cited

U.S. PATENT DOCUMENTS

| | | | | |
|---|---|---|---|---|
| 2,591,958 | * | 4/1952 | McClees | 128/882 |
| 4,336,796 | * | 6/1982 | Andrews | 128/88 |
| 4,407,277 | * | 10/1983 | Ellison | 128/882 |
| 4,440,159 | * | 4/1984 | Cochran | 128/882 |

* cited by examiner

Primary Examiner—Michael A. Brown

(74) Attorney, Agent, or Firm—Barlow, Josephs & Holmes, Ltd.

(57) ABSTRACT

An adjustable splint assembly for use in immobilizing the leg of an animal, such as a dog includes an elongated sleeve portion having a plurality of taping clips extending outwardly from opposing sides thereof, and a shaft portion slidably received within the sleeve portion such that the shaft portion and the sleeve portion are telescopically adjustable. The sleeve portion including a plurality of a set screws that extend through the sleeve to selectively engaging the shaft portion to selectively secure the shaft portion relative to the sleeve portion. In use, it is preferable to link together at least two of the splint assemblies together. In this regard, the opposing ends of the splint assembly (one on the shaft portion and one on the sleeve portion) have complementary pivot connectors such that the sleeve portion of a first splint is releasably and pivotably connectable to the shaft portion of second splint. The pivot connectors also include a single set screw that passes through one of the pivot connectors and selectively engages the surface of the opposing connector to selectively secure a relative rotational position of the pivot connectors of the respective first and second splints.

16 Claims, 4 Drawing Sheets

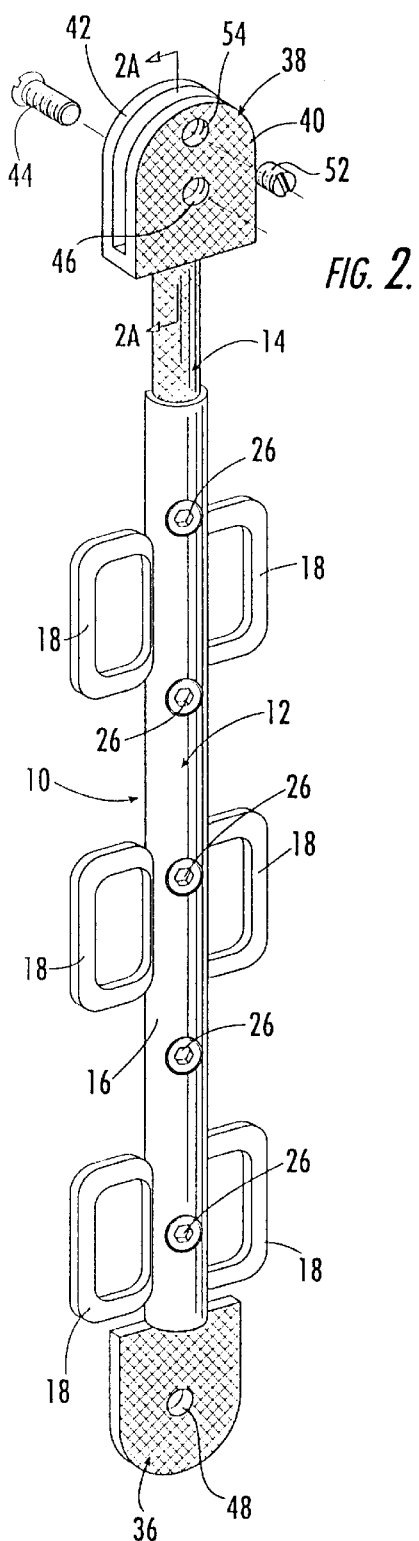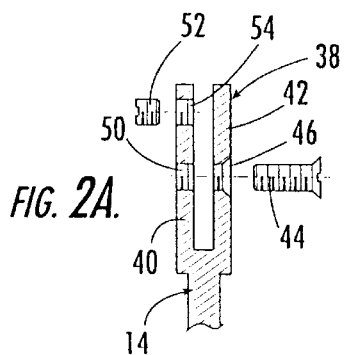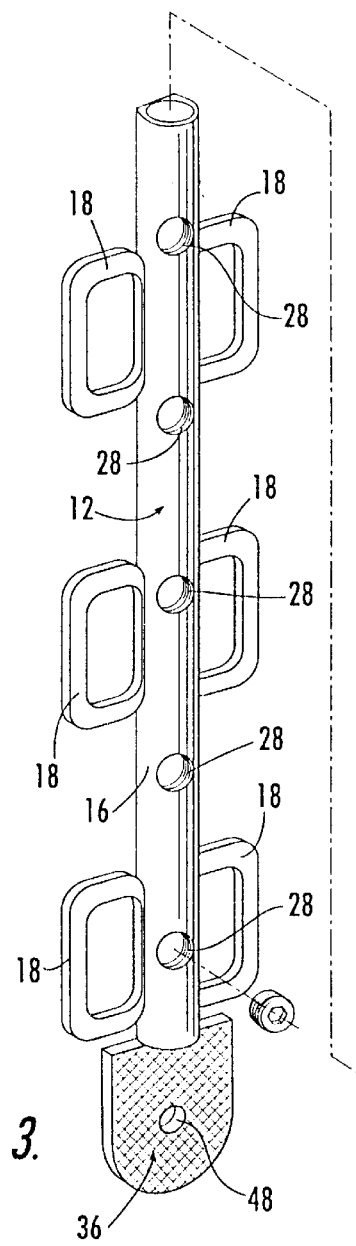

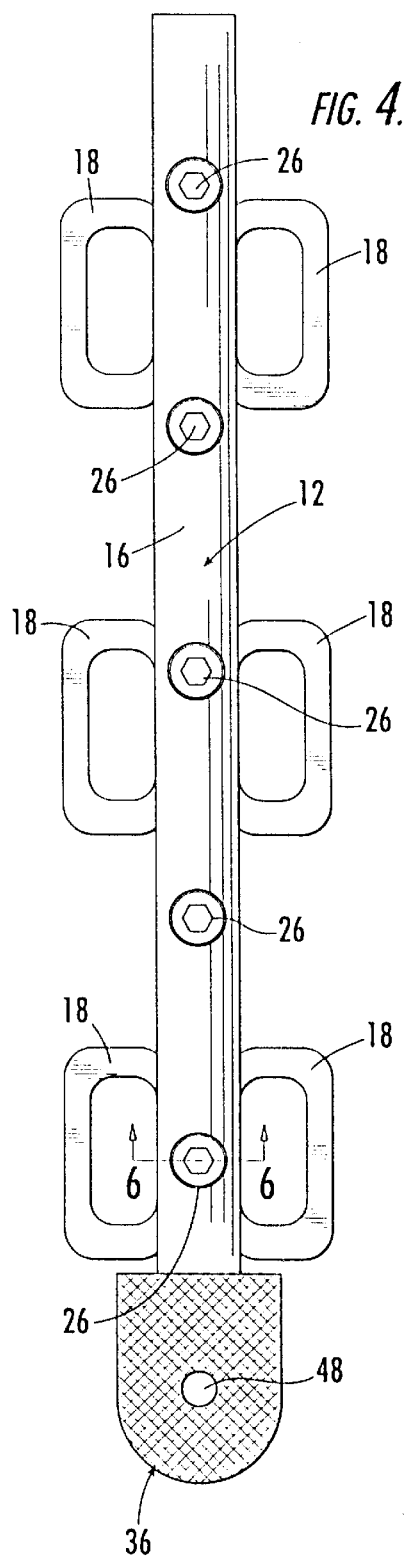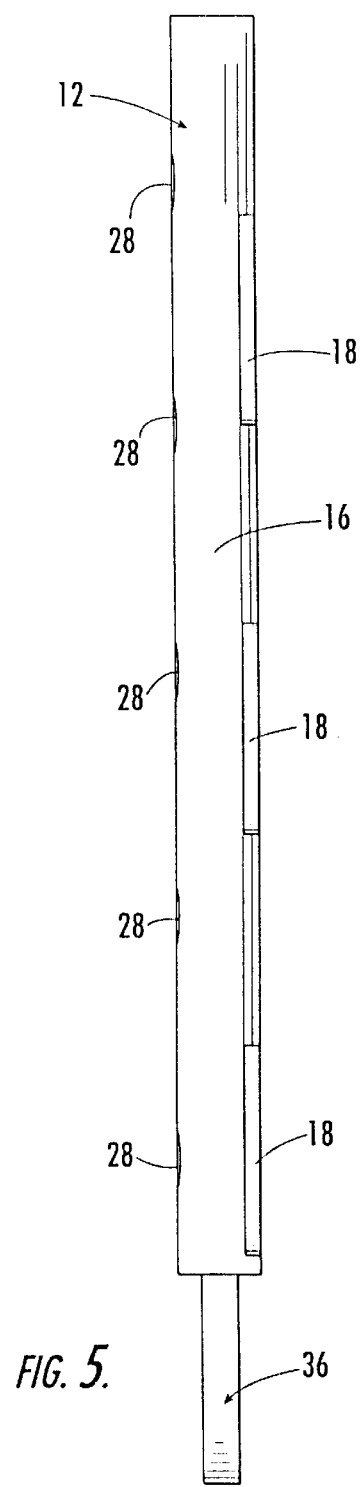
FIG. 4.
FIG. 5.

ADJUSTMENT SPLINT ASSEMBLY

BACKGROUND AND SUMMARY OF THE INVENTION

The instant invention relates to an adjustable splint assembly suitable for immobilizing the leg of an animal, such as a dog.

Animals frequently suffer orthopedic injuries, such as torn ligaments, torn tendons, broken bones, etc. Throughout the years, it has become a well established practice to use splints or casts to immobilize the limbs of both humans and animals during the recovery period. Immobilization speeds recovery and prevents further injury. The art of splinting in the veterinary orthopedic medicine has offered all kinds and shapes of splint devices for various injuries and various animals. For example, the U.S. Pat. No. to Walker et al No. 3,470,873, Carlin U.S. Pat. No. 4,424,764, McCarthy U.S. Pat. No. 4,099,525, Dawson Jr. U.S. Pat. No. 4,029,090, Clarke U.S. Pat. No. 2,016,958, Invidiato U.S. Pat. No. 2,302,868, Dowers U.S. Pat. No. 3,416,519, Nelson U.S. Pat. No. 4,361,143, Campbell U.S. Pat. No. 5,134,992, Farley U.S. Pat. No. 4,726,361, Sterling U.S. Pat. No. 4,019,504, Gledhill U.S. Pat. No. 3,745,997, Parcher U.S. Pat. No. 2,339,515, Petersen U.S. Pat. No. 5,634,437 and French U.S. Pat. No. 1,295,297 represent some of the various embodiments of the general state of the art presently known in the veterinary and medical fields. Some solutions tend to be narrowly tailored to a specific animal or size of animal. These types of narrowly tailored solutions require multiple sizes and shapes to accommodate different animals and are thus prohibitively expensive to utilize in a commercial application. Other solutions are so broad in their intended applications, that they tend to not fit any type of animal correctly. Poor fitting and difficulty in use in a practical scenario discourages use of the entire solution. Accordingly, there is believed to be a need in the field for an adjustable splint that can be easily adjusted and fitted to a wide range of sizes and types of animals.

In this regard, the instant invention provides an adjustable splint assembly for use in immobilizing the leg of an animal, such as a dog. The adjustable splint assembly includes an elongated sleeve portion having a plurality of taping clips extending outwardly from opposing sides thereof, and a shaft portion slidably received within the sleeve portion such that the shaft portion and the sleeve portion are telescopically adjustable.

The splint is intended for use over a Robert Jones type bandage wherein a lower surface of the sleeve portion is placed against the bandage and secured to the outside of the bandage by passing tape through the taping clips and around the leg of the animal. In this regard, it is noted that that lower surface of the sleeve portion is preferably planar and that the taping clips extend tangentially outwardly from the sleeve portion adjacent the lower surface. This configuration allows the sleeve portion to rest flatly against the outside surface of the bandage. The sleeve portion further includes a plurality of a set screws on an upper surface that extend through the sleeve to engage the shaft portion and selectively secure the shaft portion relative to the sleeve portion. Since the sleeve portion is preferably constructed from a plastic material to reduce weight, the area of the sleeve portion where the set screw holes are located is reinforced with an elongated metal strip. Or alternatively, each of the set screw holes can be formed by a threaded metal insert. Both of these reinforcing measures are designed to reduce stripping of the set screw threads and to thus extend the life of the splint for multiple uses.

In use, it is preferable to link together at least two, or perhaps three, of the splint assemblies together. In this regard, the opposing ends of the splint assembly (one on the shaft portion and one on the sleeve portion) include complementary pivot connectors wherein the sleeve portion of a first splint is releasably and pivotably connectable to the shaft portion of a second splint. In a preferable embodiment, the pivot connectors comprise a flange plate and a U-shaped flange having spaced flange legs which receive the flange plate therebetween. The flange plate and flange legs are pivotably connected by a removable pivot screw that passes through the elements. One of the flange legs includes a set screw that passes through the flange leg and engages the surface of the flange plate to selectively secure the relative rotational positions of the pivot connectors of the respective first and second splints.

It is also noted that the adjustable splint assembly will preferably be constructed in several different lengths, for example in 12 cm, 18 cm and 24 cm lengths to further accommodate the many different bone configurations of different animals.

Accordingly, among the objects of the instant invention are: the provision of an adjustable splint assembly; the provision of such a splint assembly that is adjustable in length; the provision of an adjustable splint assembly that can be pivotably linked together in multiple sections to form a multi-segmented splint assembly; the provision of such a splint assembly that has an adjustable angle of rotation between linked splint assemblies; the provision of such a splint assembly that is light weight in construction; the provision of such a splint assembly that is suitable for use over a conventional Robert Jones Bandage; and the provision of such a splint assembly that includes multiple taping clips for securing the splint to the animal's limb.

Other objects, features and advantages of the invention shall become apparent as the description thereof proceeds when considered in connection with the accompanying illustrative drawings

DESCRIPTION OF THE DRAWINGS

In the drawings which illustrate the best mode presently contemplated for carrying out the present invention:

FIG. 2 is a perspective view of the adjustable splint assembly;

FIG. 2A is a cross-sectional view of the end connector as taken along line 2A–2A of FIG. 2;

FIG. 3 is an exploded assembly view of the adjustable splint;

FIG. 4 is a front view of the sleeve portion;

FIG. 5 is a side view thereof;

DESCRIPTION OF THE PREFERRED EMBODIMENT

Figure 1:
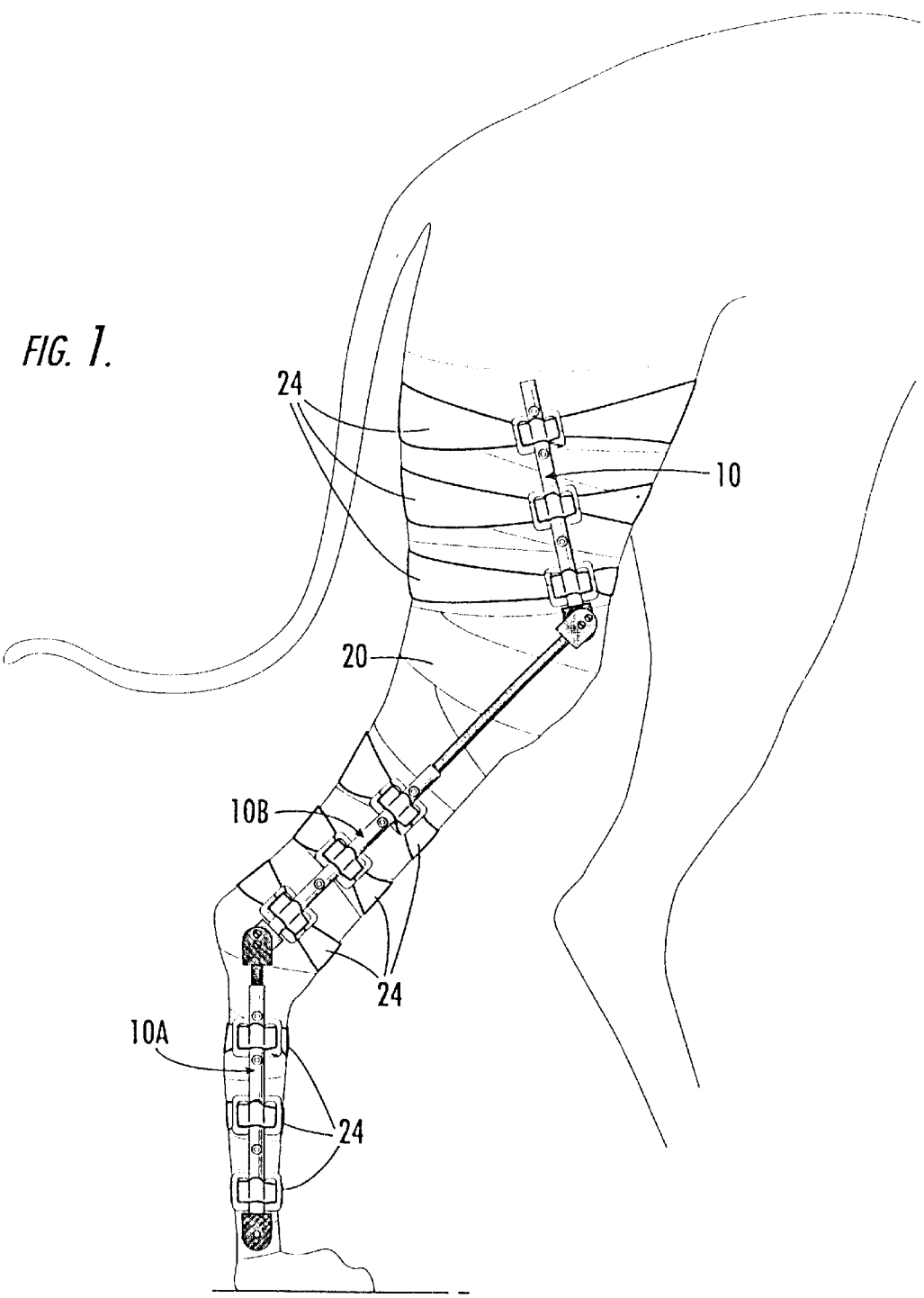
FIG. 1 is an elevational view of the rear leg of a dog showing application of several sections of the adjustable splint assembly of the present invention secured over a Robert Jones bandage.
Figure 6:
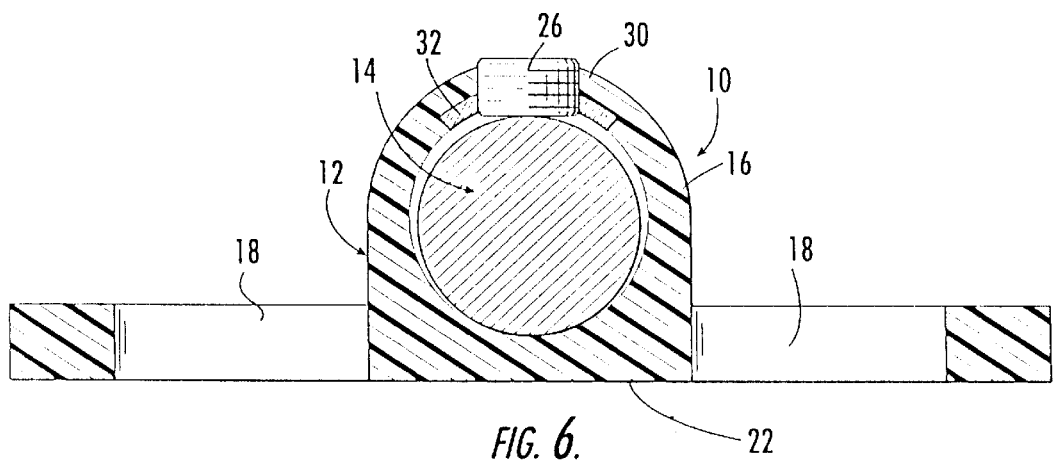
FIG. 6 is a cross-sectional view of the sleeve as taken along line 6—6 of FIG. 4.
Figure 7:
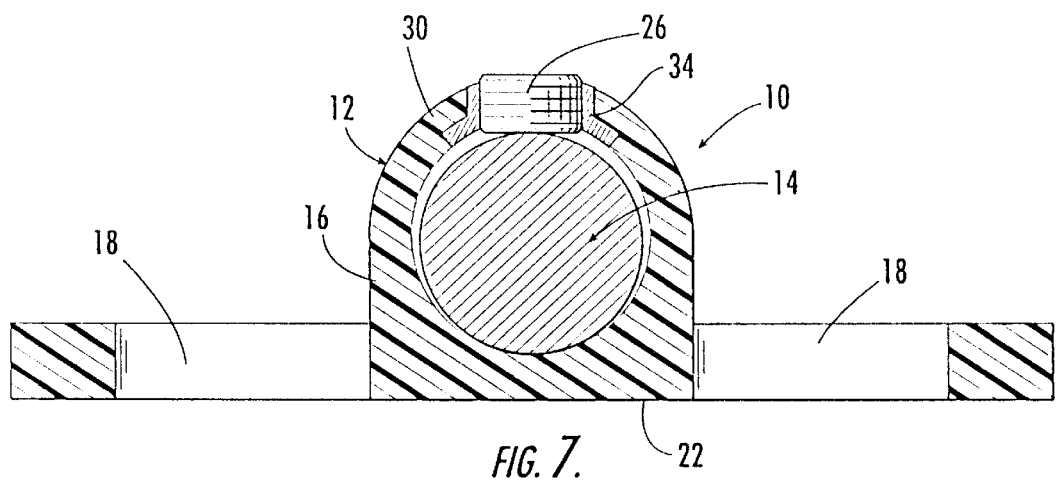
FIG. 7 is another cross-sectional view showing an alternative set screw anchoring system.

Referring now to the drawings, the adjustable splint assembly of the instant invention is illustrated and generally indicated at 10 in FIGS. 1–7. As will hereinafter be more fully described, the adjustable splint assembly 10 is particularly suited for use in immobilizing the leg of an animal, such as a dog. The splint assembly 10 is adjustable in length to accommodate the different lengths of leg bones found in different types of animals, and multiple splits can be pivotably linked together to provide the proper angular configurations required for proper healing and recovery.

The adjustable splint assembly 10 includes an elongated sleeve portion generally indicated at 12 and a shaft portion generally indicated at 14. Both the sleeve portion 12 and the shaft portion 14 are preferably molded from a high density, light-weight plastic material, such as a high-impact polyethylene plastic. However, other metal materials could also be utilized, and it should thus be understood that the scope of the invention is not intended to be limited by the selection of materials for construction of the elements.

The sleeve portion 12 includes an elongated hollow body portion 16, and a plurality of taping clips 18 that extending outwardly from opposing sides of the body portion 16 in symmetrically opposed relation. The shaft portion 14 is slidably received within the sleeve portion 12 such that the shaft portion 14 and the sleeve portion 12 are telescopically adjustable.

Referring to FIG. 1, the splint assembly 10 is intended for use over a Robert Jones type bandage 20 wherein a lower surface 22 of the sleeve portion 12 is placed against the bandage 20 and secured to the outside of the bandage 20 by passing tape strips 24 through the taping clips 18 and around the leg of the animal. In this regard, it is noted that that lower surface 22 of the sleeve portion is preferably planar and that the taping clips 18 extend tangentially outwardly from the sleeve portion 12 adjacent the lower surface 22 (See FIGS. 5–6). This configuration allows the sleeve portion 12 to rest flatly against the outside surface of the bandage 20. The sleeve portion 12 further includes a plurality of a set screws 26 that extend through threaded set screw openings 28 in an upper surface 30 of the sleeve portion 12 to engage the shaft portion 14 and selectively secure the shaft portion 14 relative to the sleeve portion 12. The outer surface of the shaft portion 14 is preferably knurled or provided with serations to improve engagement of the set screw and prevent slipping of the shaft portion 14 relative to the sleeve portion 12 once the splint assembly 10 is in position. Since the sleeve portion 12 is preferably constructed from a plastic material to reduce weight, the area of the sleeve portion 12 where the set screw holes 28 are located is reinforced with an elongated metal strip 32 (see FIG. 6). The strip 32 can be imbedded into the plastic during the molding process, or can be inserted into the sleeve portion 12 after molding. The set screw openings 28 are preferably tapped to threadably receive the set screws 26, with the added metal strip 32 being intended to reduce stripping of the openings 28, thus allowing the device 10 to be re-used multiple times. As an added benefit, the set screws 26 further act as radio opaque indicators for reference radiographs after application of the splint assembly 10.

Alternatively, each of the set screw holes 28 can be formed by a threaded metal insert 34 imbedded within the plastic (see FIG. 8). Both of the metal reinforcing measures are designed to reduce stripping of the set screw threads and to thus extend the useful life of the splint assembly 10.

In use, it is preferable to link together at least two, or perhaps three, of the splint assemblies 10 together (See FIG. 1). In this regard, the opposing ends of the splint assembly 10 (one on the shaft portion and one on the sleeve portion) include complementary pivot connectors wherein the shaft portion 14 of a first splint 10A is releasably and pivotably connectable to the sleeve portion 12 of a second splint 10B, or vice versa. In the preferable embodiment, the pivot connectors comprise a flange plate generally indicated at 36 on the end of the sleeve portion 12 and a U-shaped flange generally indicated at 38 on the end of the shaft portion 14. The U-shaped flange 38 includes spaced flange legs 40, 42 which receive the flange plate 36 therebetween. The flange plate 36 and flange legs 40, 42 are pivotably connected by a removable pivot screw 44 that passes through an opening 46 in flange leg 42, through an opening 48 in flange plate 36, and is secured in a threaded opening 50 the opposing flange leg 40. This allows the central flange plate 36 to rotate or pivot relative to the outer flange legs 40, 42. Flange leg 40 includes a set screw 52 that passes through a threaded opening 54 in the flange leg and engages the surface of the flange plate 36 to selectively secure the relative rotational positions of the pivot connectors of the respective first and second splints 10A, 10B. The outer surface of the flange plate 36 is preferably knurled or provided with serations to improve engagement of the set screw 52 and prevent rotation once the splint 10 is in position.

It is noted that the adjustable splint assembly 10 will preferably be constructed in several different lengths, for example in 12 cm, 18 cm and 24 cm lengths to further accommodate the many different bone configurations of different animals. The preferred embodiment as illustrated in the drawing figures is a representative illustration of a 18 cm version of the splint assembly 10. Referring to FIG. 1, there is shown a application of several linked splint assemblies 10A, 10B, 10C to immobilize the leg of a larger dog, such as a greyhound. The three separate splint assemblies 10A, 10B, 10C are linked end to end to provide the proper support. The lowermost splint assembly 10A is an 18 cm length section and is not extended in length. In this case, the lower portion of the leg is approximately the same length of the 18 cm splint so that no extension is required. In smaller dogs, or other animals, a shorter length splint 10, such as the 12 cm length may be more appropriate. The center splint assembly 10B is extended to its full length to accommodate the longer span of the middle leg portion. In this case, an 18 cm splint was utilized, although a longer 24 cm length would also have been effective. The uppermost splint 10C is another 18 cm splint section and it is noted that the shaft portion 14 is not included since there is no need to link the upper end of the splint assembly 10C. The three splint assemblies 10A, 10B, 10C are linked and pivotally secured in position as described hereinabove.

It can therefore be seen that the present invention provides a unique, and effective splint assembly 10. The splint assembly 10 is simple in construction, easy to assemble and adjust and versatile for application to almost any size animal. The design provides for the combination of any number and size of the splint assemblies 10, and significantly aids in the positioning of limbs in virtually any anatomically correct position. The splint assembly 10 can be used as a rigid point to brace the limb against the abdominal or thoracic body if needed, and rear limbs can be stabilized to each other across the lower portion of the spinal column in the event of a pelvic fracture. Luxated joints can also be stabilized by utilizing the torso of the animal for support. The ability to link the splint assemblies 10 together, to adjust the rotational angle of the splint assemblies 10 with respect to each other, and the ability to change the lengths of the individual splint segments 10 is critical to the versatile function of the invention. Rotational adjustment is a tremendous benefit in being able to allow for slight hyperextension of the joint during recovery, promoting rapid and complete recovery while counteracting muscle atrophy. Because the splint assembly 10 can be constructed from lightweight, high strength plastic, the splint assembly 10 is light in weight and does not become an added weight burden on the animal during the recovery period. For these reasons, the instant invention is believed to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An adjustable splint assembly comprising:
   an elongated sleeve portion having first and second ends, said sleeve portion having a plurality of taping clips extending outwardly from opposing sides thereof;
   a shaft portion having first and second ends, said first end of said shaft portion being slidably received within said second end of said sleeve portion such that said shaft portion and said sleeve portion are telescopically adjustable,
   a first fastener element on said sleeve portion, said first fastener selectively engaging said shaft portion to selectively secure said shaft portion relative to said sleeve portion;
   a first pivot connector at said first end of said sleeve portion;
   a second pivot connector at said second end of said shaft portion, said first and second pivot connectors comprising complementary interfitting pivot connectors such that the first end of the sleeve portion of a first splint is releasably and pivotably connectable to the second end of the shaft portion of second splint; and
   a second fastener element on one of said first and second pivot connectors, said second fastener element selectively engaging the other of the said first and second pivot connector elements to selectively secure a relative rotational position of said first and second pivot connectors of respective first and second splints.

2. The adjustable splint assembly of claim 1 wherein said taping slips extend outwardly from said sleeve portion in symmetrically opposed relation.

3. The adjustable splint assembly of claim 1 wherein said sleeve portion has upper and lower opposed surfaces, said lower surface being received against a bandaged leg to be immobilized.

4. The adjustable splint assembly of claim 3 wherein said taping clips extend outwardly from said sleeve portion in symmetrically opposed relation.

5. The adjustable splint assembly of claim 4 wherein said taping clips extend tangentially outwardly from said sleeve portion adjacent said lower surface thereof.

6. The adjustable splint assembly of claim 3 wherein said taping clips extend tangentially outwardly from said sleeve portion adjacent said lower surface thereof.

7. The adjustable splint assembly of claim 3 wherein said first fastener element comprises a set screw threadably received into a complementary threaded bore in said upper surface of said sleeve portion, said set screw extending through said sleeve portion to engage with an outer surface of said shaft portion.

8. The adjustable splint assembly of claim 7 wherein said sleeve portion is constructed of a plastic material and includes a longitudinally extending metal reinforcing plate, said reinforcing plate being imbedded within the upper surface of the sleeve portion, said set screw extending through said metal reinforcing plate.

9. The adjustable splint assembly of claim 3 wherein said first and second pivot connectors respectively comprise a flange plate, and a U-shaped flange having spaced flange legs, said plate being receivable between said flange legs, said adjustable splint further comprising a pivot element received through respective pivot openings in said flange plate and said flange legs.

10. The adjustable splint assembly of claim 9 wherein said flange plate and said flange legs extend in a plane that is parallel to said lower surface of said sleeve portion.

11. The adjustable splint assembly of claim 9 wherein said second fastener element comprises a set screw threadably received through a complementary threaded opening in one of said flange legs, said set screw extending through said flange leg to engage with an outer surface of said flange plate to selectively secure the rotational position of said flange plate relative to said flange legs.

12. The adjustable splint assembly of claim 1 wherein said first fastener element comprises a set screw threadably received into a complementary threaded bore in said sleeve portion, said set screw extending through said sleeve portion to engage with an outer surface of said shaft portion.

13. The adjustable splint assembly of claim 12 wherein said sleeve portion is constructed of a plastic material and includes a longitudinally extending metal reinforcing plate, said set screw extending through said metal reinforcing plate.

14. The adjustable splint assembly of claim 12 wherein said sleeve portion is constructed of a plastic material, said threaded bore in said sleeve portion comprising a metal reinforcing insert, said set screw extending through said metal reinforcing insert.

15. The adjustable splint assembly of claim 1 wherein said first and second pivot connectors respectively comprise a flange plate, and a U-shaped flange having spaced flange legs, said plate being receivable between said flange legs, said adjustable splint further comprising a pivot element received through respective pivot openings in said flange plate and said flange legs.

16. The adjustable splint assembly of claim 15 wherein said second fastener element comprises a set screw threadably received through a complementary threaded opening in one of said flange legs, said set screw extending through said flange leg to engage with an outer surface of said flange plate to selectively secure the rotational position of said flange plate relative to said flange legs.

* * * * *